United States Patent [19]

Fozzard et al.

[11] 4,016,049

[45] Apr. 5, 1977

[54] SEPARATION OF PHENOL-CYCLOHEXANONE AZEOTROPE BY EXTRACTIVE DISTILLATION WITH ADIPIC ACID DIESTER

[75] Inventors: George B. Fozzard; Robert A. Paul, both of Bartlesville, Okla.

[73] Assignee: Phillips Petroleum Company, Bartlesville, Okla.

[22] Filed: July 28, 1976

[21] Appl. No.: 709,367

[52] U.S. Cl. .................. 203/60; 260/586 P; 260/621 A; 260/621 C

[51] Int. Cl.$^2$ .................. B01D 3/40; C07C 37/22

[58] Field of Search .......... 203/38, 60; 260/586 P, 260/621 A, 621 C, 586 AB, 586 R, 621 G

[56] References Cited

UNITED STATES PATENTS

| | | | |
|---|---|---|---|
| 2,265,939 | 12/1941 | Field | 202/42 |
| 2,360,859 | 10/1944 | Evans | 196/13 |
| 2,762,760 | 9/1956 | Walker | 202/39.5 |
| 2,865,819 | 12/1958 | Hagemeyer | 202/42 |
| 2,986,583 | 5/1961 | Robbers | 260/621 A |
| 3,169,101 | 2/1965 | Berthoux | 202/39.5 |
| 3,492,362 | 1/1970 | Netteshein | 260/666 |
| 3,630,855 | 12/1971 | Turbin | 260/621 A |

*Primary Examiner*—Hiram H. Bernstein

[57] ABSTRACT

Phenol-cyclohexanone azeotrope, for example, resulting from the cleavage product of 1-phenylcyclohexylhydroperoxide resulting from the oxidation of cyclohexylbenzene, from which cyclohexylbenzene may have been separated, is subjected to an extractive distillation with a selective solvent essentially containing a diester of adipic acid, e.g. a dialkyl and/or a dicycloalkyl ester of adipic acid. Specifically disclosed is a separation of a cyclohexanone-phenol mixture employing di(2-ethylhexyladipate). The diesters up to and including diC$_{14}$ are referenced.

5 Claims, No Drawings

SEPARATION OF PHENOL-CYCLOHEXANONE AZEOTROPE BY EXTRACTIVE DISTILLATION WITH ADIPIC ACID DIESTER

This invention relates to the separation of a phenol-cyclohexanone azeotrope. In one of its aspects, it relates to an extractive distillation separation of a mixture containing phenol-cyclohexanone azeotrope. In a more specific aspect the invention relates to a process for recovering cyclohexanone on the one hand and phenol on the other form a mixture containing these compounds, for example, from a mixture resulting from cleavage of 1-phenyl-cyclohexylhydroperoxide as obtained by the oxidation of cyclohexylbenzene.

In one of its concepts the invention provides a process for the separation of a mixture containing phenol, cyclohexanone, and which may contain cyclohexylbenzene by subjecting the same to conditions of extractive distillation with a selective solvent essentially comprising a diester of adipic acid. In another of its concepts the invention relates to such a separation by extractive distillation of a mixture resulting from a cleavage of 1-phenyl-cyclohexylhydroperoxide obtained by the oxidation of cyclohexylbenzene. In a further concept of the invention the diester of adipic acid can be a dialkyl and/or a dicycloalkyl ester.

It is an object of this invention to provide a process for the separation of a mixture containing phenol and cyclohexanone. It is another object of the invention to provide a process for the extractive distillation of a mixture containing phenol and cyclohexanone which mixture may contain some cyclohexylbenzene. It is a further concept of the invention to provide a selective solvent, which may be modified by further solvents or co-solvents, for the extractive distillation separation of phenol and cyclohexanone.

Other aspects, concepts, objects, and several advantages of the invention are apparent from a study of this disclosure and the appended claims.

According to the present invention there is provided a process for the separation of a mixture containing phenol, cyclohexanone, and possibly cyclohexylbenzene which comprises subjecting said mixture to an extractive distillation operation in which an extractive solvent is employed and which essentially is a diester of adipic acid.

Solvents useful for the invention are the dialkyl and dicycloalkyl esters of an adipic acid of the general formula $(CH_2CH_2CO_2R)_2$ where R can be an alkyl or cycloalkyl group containing up to 14 carbon atoms. Examples include dimethyl dibutyl, diisobutyl, di(2-ethylhexyl), didecyl, dicyclohexyl, bis(2-cyclohexyl ethyl), and bis(4-butylcyclohexyl) adipates.

Extractive distillations according to the concept of the invention were conducted in a ¾-inch diameter packed column 3 feet long.

EXAMPLE 1

A 70–30 weight percent mixture of phenol-cyclohexanone, which is an azeotropic mixture boiling at 122° C at 100 mm Hg absolute pressure was fed to the column near the mid-point at a rate of 1 cc/min at a temperature of 149° C. Di(2-ethylhexyl) adipate solvent was introduced near the top of the column at a rate of 1.4 cc/min at a temperature of 95° C. Overhead product was taken off at an average rate of 0.3 cc/min and averaged 98 percent cyclohexanone purity with no detectable solvent. Accumulated kettle product was 89 percent phenol on a solvent-free basis.

EXAMPLE 2

A mixture composed of 32 percent cyclohexanone, 66 percent phenol and 2 percent cyclohexylbenzene was fed at about the mid-point of the extractive distillation column operating at 50 mm Hg absolute pressure at a rate of 1 cc/min and a temperature of 144° C. Di(2-ethylhexyl) adipate solvent was introduced near the top of the column at a rate of 1.6 cc/min at a temperature of 92° C. Overhead product was about 99.7 percent cyclohexanone, 0.3 percent phenol and contained no cyclohexylbenzene. Accumulated kettle product was 91 percent phenol, 6 percent cyclohexanol and 3 percent cyclohexylbenzene.

Reasonable variation and modification are possible within the scope of the foregoing disclosure and the appended claims to the invention the essence of which is that a diester of adipic acid, as disclosed, has been found to be an effective extractive distillation solvent by the extractive distillation of cyclohexanone-phenol containing mixtures.

We claim:

1. A process for the separation by extractive distillation of a cyclohexanone and phenol containing mixture which comprises subjecting the mixture to extractive distillation conditions in the presence of an adipic acid diester extractive distillation agent.

2. A process according to claim one wherein the diester is at least one of a dialkyl and dicycloalkyl ester of adipic acid.

3. A process according to claim one wherein the diester of adipic acid has the general formula $(CH_2CH_2CO_2R)_2$ where R can be an alkyl or cycloalkyl group containing up to 14 carbon atoms.

4. A process according to claim one wherein the diester of adipic acid is at least one selected from the following: dimethyl, dibutyl, diisobutyl, di(2 ethylhexyl), didecyl, dicyclohexyl, bis(2-cyclohexyl ethyl) and bis(4-butylcyclohexyl) adipates.

5. A process according to claim one wherein the phenol and cyclohexanone containing mixture results from a cleavage of the oxidation product obtained upon oxidizing cyclohexylbenzene.

* * * * *